(12) United States Patent
Karakossian

(10) Patent No.: US 9,333,208 B2
(45) Date of Patent: May 10, 2016

(54) HCN INHIBITORS AFFECTING GANGLION CELL FUNCTION AND VISUAL FUNCTION

(71) Applicant: Allergan, Inc., Irvine, CA (US)

(72) Inventor: Movses H. Karakossian, Foothill Ranch, CA (US)

(73) Assignee: Movses H. Karakossian, Pasadena, CA (US)

( * ) Notice: Subject to any disclaimer, the term of this patent is extended or adjusted under 35 U.S.C. 154(b) by 16 days.

(21) Appl. No.: 14/327,786

(22) Filed: Jul. 10, 2014

(65) Prior Publication Data

US 2015/0025062 A1    Jan. 22, 2015

Related U.S. Application Data

(60) Provisional application No. 61/846,912, filed on Jul. 16, 2013.

(51) Int. Cl.
| | |
|---|---|
| *A61K 31/55* | (2006.01) |
| *A61K 31/505* | (2006.01) |
| *A61K 9/00* | (2006.01) |
| *A61K 45/00* | (2006.01) |
| *A61K 31/415* | (2006.01) |

(52) U.S. Cl.
CPC ............... *A61K 31/55* (2013.01); *A61K 9/0048* (2013.01); *A61K 31/415* (2013.01); *A61K 31/505* (2013.01); *A61K 45/00* (2013.01)

(58) Field of Classification Search
CPC ............................. A61K 31/55; A61K 31/505
USPC ....................................... 514/212.07, 31, 505
See application file for complete search history.

(56) References Cited

U.S. PATENT DOCUMENTS

| | | | | |
|---|---|---|---|---|
| 8,076,305 | B2 * | 12/2011 | Sigg et al. | 514/44 R |
| 8,236,296 | B2 * | 8/2012 | Rosen et al. | 424/93.21 |
| 2004/0033943 | A1 * | 2/2004 | Strijbos et al. | 514/12 |
| 2004/0115668 | A1 * | 6/2004 | Folander et al. | 435/6 |

* cited by examiner

*Primary Examiner* — Raymond Henley, III
(74) *Attorney, Agent, or Firm* — One3 IP Management, P.C.; Dean G. Statbakis; Peter D. Weinstein

(57) ABSTRACT

The present invention is directed to a method of enhancing visual function in a subject, comprising administering to the subject in need of such enhancement, a therapeutically effective amount of an inhibitor of a hyperpolarization-activated cyclic nucleotide-gated (HCN) channel. The present invention is also directed to an ocular implant comprising a therapeutically effective amount of the HCN channel inhibitor.

19 Claims, 12 Drawing Sheets

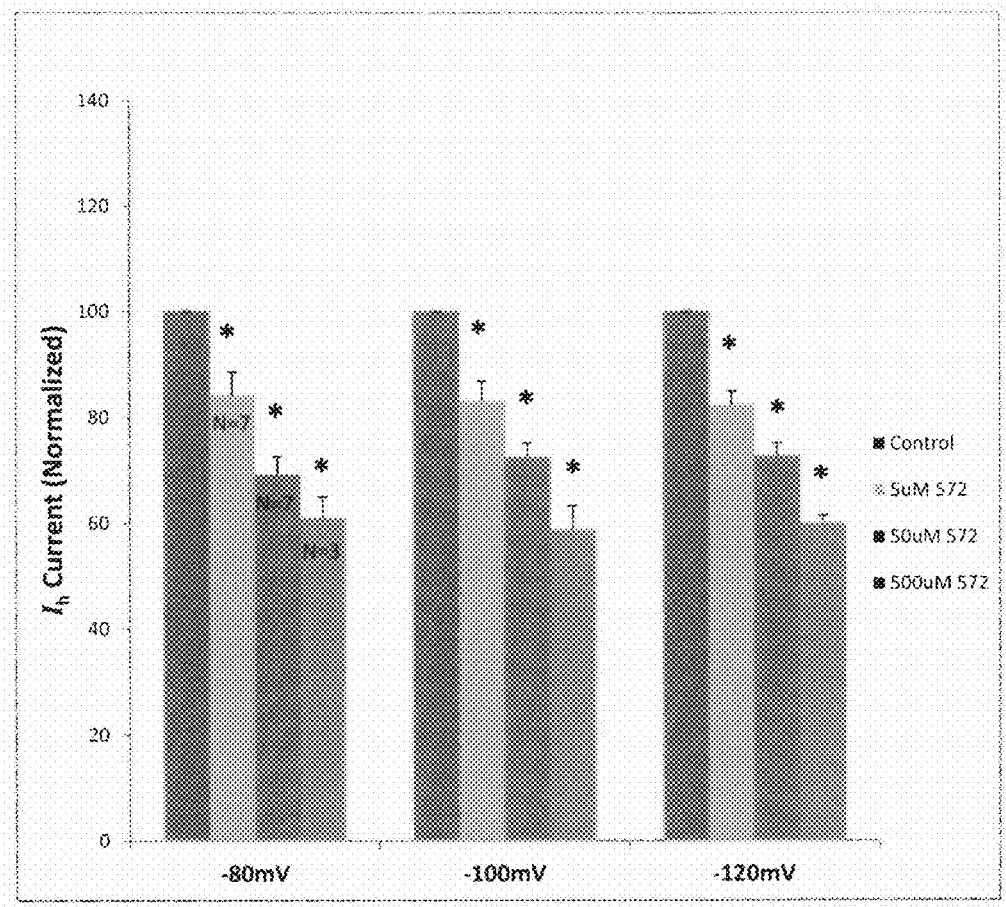

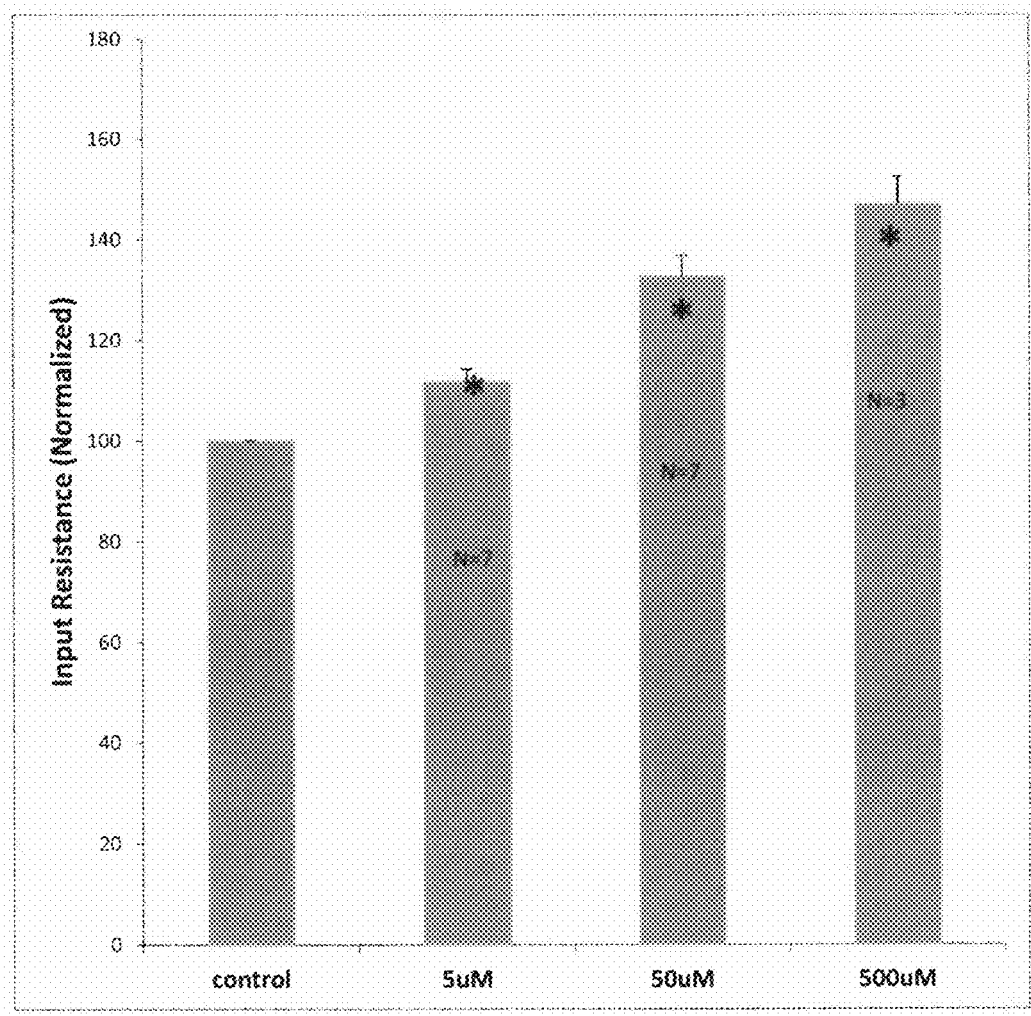

HCN INHIBITORS AFFECTING GANGLION CELL FUNCTION AND VISUAL FUNCTION

CROSS REFERENCE TO RELATED APPLICATIONS

This application claims the benefit of U.S. Provisional Application Ser. No. 61/846,912 filed on Jul. 16, 2013 of which is incorporated by reference herein in its entirety.

FIELD OF THE INVENTION

The present invention is directed to methods of enhancing visual function and for treating ocular conditions resulting from low or poor visual function by administration of an inhibitor of hyperpolarization-activated cyclic nucleotide-gated (HCN) channel.

BACKGROUND OF THE INVENTION

Hyperpolarization-activated Cyclic Nucleotide gated (HCN) were identified in the late 1970s and early 1980s in sinoatrial node cells and neurons, respectively (Brown et al., 1979; halliwell and Adams, 1982). HCN channels are members of the pore loop cation channels superfamily (yu et al., 2005). In mammals the HCN channel family includes 4 members (HCN1-4) that are differentially expressed in different types of excitable tissues (for review see: Biel et al., 2009; Kaup and Seifert, 2001) and share approximately 60% sequence identity with each other and are present in all vertebrates (Ludwig et al., 1998). HCN channels form tetrameric complexes consisting of homomeric or heteromeric subunit compositions with each subunit consisting of six transmembrane alpha helices. Similar to other voltage-gated channels, HCN channels possess voltage sensors (Manniko et al., 2002). HCN channels are activated by membrane hyperpolarization and upon opening give rise to a depolarizing mixed cation current termed $I_h$, $I_f$ or $I_q$, which cause the re-depolarization of the membrane potential to near resting potentials. HCN channels contain a cyclic nucleotide binding domain in the carboxyl terminus. Following the binding of cyclic AMP or cyclic GMP, the activation kinetics of the channels are shifted to become more sensitive to membrane hyperpolarization (Wainger et al., 2001). Aside from their role as pacemakers in the sino-atrial node of the heart, HCN channels perform important functions in neuronal cells including determination of resting membrane potential, dendritic integration, action potential rhythmicity, synaptic transmission and synaptic plasticity (for review see: Robinson and Siegelbaum, 2003).

Different HCN channel subtypes are expressed throughout the central nervous system (Biel et al., 2009) including the retina where all isoforms are expressed, with HCN1 and HCN4 showing dominant expression (Muller et al., 2003). HCN1 is expressed in all major retinal neuronal subtypes whereas HCN4 is expressed predominantly in bipolar and ganglion cell (Stradleigh et al., 2011). Targeted deletion of HCN1 from the mouse retina results in prolonged light responses as seen in electroretinogram flicker responses suggesting an important function of these channels in rod and cone photoreceptors since B-wave amplitude, which result from ON-bipolar cell function, remained unaltered, or slightly reduced in these animals (Knop et al., 2008). Both HCN1 and HCN4 are expressed in retinal ganglion cells where most cells show a mosaic of expression pattern (Stradleigh et al., 2011). Although strongly expressed in ganglion cells, the function of these channels in ganglion cells and overall visual physiology is unclear.

WO2011000915A1 refers to isoform-selective HCN blockers.

U.S. Pat. No. 8,076,325 B2 refers to 1,2,4,5-tetrahydro-3H-benzazepine compounds as blockers of HCN channels, a process for their preparation and pharmaceutical compositions containing them.

WO 2008/121735 refers to methods of identifying modulators of HCN channels.

BIBLIOGRAPHY

Biel M, Wahl-Schott C, Michalakis S, Zong X (2009) Hyperpolarization-activated cation channels: from genes to function. Physiol Rev 89:847-885.

Brown H, Difrancesco D, Noble S (1979) Cardiac pacemaker oscillation and its modulation by autonomic transmitters. J Exp Biol 81:175-204.

Guire E S, Lickey M E, Gordon B (1999) Critical period for the monocular deprivation effect in rats: assessment with sweep visually evoked potentials. J Neurophysiol 81:121-128.

Halliwell J V, Adams P R (1982) Voltage-clamp analysis of muscarinic excitation in hippocampal neurons. Brain Res 250:71-92.

Kaupp U B, Seifert R (2001) Molecular diversity of pacemaker ion channels. Annu Rev Physiol 63:235-257.

Knop G C, Seeliger M W, Thiel F, Mataruga A, Kaupp U B, Friedburg C, Tanimoto N, Muller F (2008) Light responses in the mouse retina are prolonged upon targeted deletion of the HCN1 channel gene. Eur J Neurosci 28:2221-2230.

Ludwig A, Zong X, Jeglitsch M, Hofmann F, Biel M (1998) A family of hyperpolarization-activated mammalian cation channels. Nature 393:587-591.

Mannikko R, Elinder F, Larsson H P (2002) Voltage-sensing mechanism is conserved among ion channels gated by opposite voltages. Nature 419:837-841.

Muller F, Scholten A, Ivanova E, Haverkamp S, Kremmer E, Kaupp U B (2003) HCN channels are expressed differentially in retinal bipolar cells and concentrated at synaptic terminals. Eur J Neurosci 17:2084-2096.

Norcia A M, Tyler C W (1985) Spatial frequency sweep VEP: visual acuity during the first year of life. Vision Res 25:1399-1408.

Ridder W H, 3rd (2004) Methods of visual acuity determination with the spatial frequency sweep visual evoked potential. Doc Ophthalmol 109:239-247.

Robinson R B, Siegelbaum S A (2003) Hyperpolarization-activated cation currents: from molecules to physiological function. Annu Rev Physiol 65:453-480.

Stradleigh T W, Ogata G, Partida G J, Oi H, Greenberg K P, Krempely K S, Ishida A T (2011) Colocalization of hyperpolarization-activated, cyclic nucleotide-gated channel subunits in rat retinal ganglion cells. J Comp Neurol 519:2546-2573.

Wainger B J, DeGennaro M, Santoro B, Siegelbaum S A, Tibbs G R (2001) Molecular mechanism of cAMP modulation of HCN pacemaker channels. Nature 411:805-810.

Yu H, Chang F, Cohen I S (1995) Pacemaker current i(f) in adult canine cardiac ventricular myocytes. J Physiol 485 (Pt 2):469-483.

SUMMARY OF THE INVENTION

The present invention provides a method of enhancing visual function in a subject, comprising administering to the subject in need of such enhancement, a therapeutically effective amount of a compound that is an inhibitor of a hyperpolarization-activated cyclic nucleotide-gated (HCN) channel.

The present invention also provides a method of treating an ocular condition resulting from low/poor visual function in a subject, comprising administering to said subject in need of such treatment, a therapeutically effective amount of a compound that is an inhibitor of a hyperpolarization-activated cyclic nucleotide-gated (HCN) channel.

The present invention also provides an ocular implant comprising a therapeutically effective amount of a compound that is an inhibitor of a hyperpolarization-activated cyclic nucleotide-gated (HCN) channel.

BRIEF DESCRIPTION OF THE DRAWINGS

FIG. 11 shows the effect of different concentrations of Ivabradine on retinal ganglion cell HCN ($I_h$) current. Ganglion cell were voltage clamped at −60 mV and stepped to −80, −100 and −120mV for 1 second. The HCN mediated current was recorded (control) and different concentrations of Ivabradine were perfused into the recording chamber with every concentration at every voltage step there was statistically significant decrease in the HCN mediated current as compared to control (indicated by asterisks).

FIG. 12 shows the effect of different concentrations of Ivabradine on Retinal ganglion cell input resistance. Ganglion cell were voltage clamped at −60 mV and stepped to −55 mV. The steady-state current was recorded and the input resistance of the ganglion cell was calculated using Ohms law (V=IR). The input resistance of the ganglion cell increased with every concentration of Ivabradine in a linear manner as compared to control (asterisks indicate statistical significance).

DETAILED DESCRIPTION OF THE INVENTION

Embodiments of the Invention

Vision is composed of many simultaneous functions. If vision is normal, seeing is so effortless that we do not notice the different visual functions.

The different components of the visual image are: forms, colors and movement. Thus we have form perception, color perception and motion perception.

We see both during the day light and during very dim light. In day light, photopic vision, we perceive colors because of function of the cone cells; in very dim light, scotopic vision, we see only shades of gray, since rod cells respond only to luminance differences. In twilight, when both rod and cone cells function, we have mesopic vision.

Vision is measured with many different tests, such as tests for visual acuity, visual field, contrast sensitivity, color vision, visual adaptation to different luminance levels, binocular vision and stereoscopic vision.

The term "visual function" as used herein includes all of the above, namely visual acuity, visual field, contrast sensitivity, color vision, visual adaptation to different luminance levels, binocular vision and three dimensional (stereoscopic) vision.

In another embodiment of the present invention, the visual function is visual acuity.

A good article on different visual functions is available on the web at http://www.lea-test.fi/en/eyes/visfunct.html.

Figure 1:
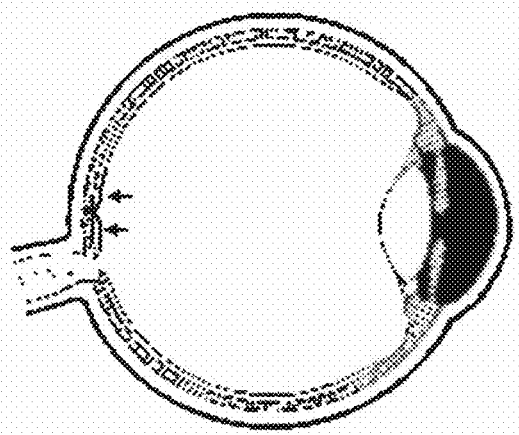
FIG. 1 shows that in the middle of the retina there is a small pit, the fovea, with which we see sharply. Only a few millimeters from the fovea (arrows) the visual acuity is 20/200 (6/60 or 0.1) even in a normal person.

"Visual acuity" is measured with visual acuity charts at distance and at near. The test measures what is the smallest letter, number or picture size that the patient still sees correctly. Visual acuity is good only in the very middle of the retina. See FIG. 1.

Figure 2:
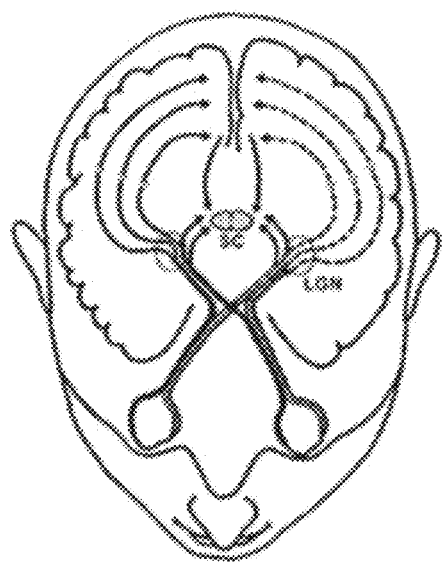
FIG. 2 shows the visual pathways from the eyes to the visual cortex. Note that there are also connections to the central parts of the brain. Note also that in the optic radiation, the pathway from the LGN (lateral geniculate nucleus) to the primary visual cortex there are marked arrows in the direction from the primary visual cortex to the LGN. Actually, there are some ten times more fibres bringing information from the primary visual cortex to the LGN than in the opposite direction. From the primary visual cortex information flows "backwards" also to the superior colliculus (SC).

When a person with normal vision looks straight forward without moving the eyes, (s)he sees also on both sides. The area visible at once, without moving the eyes, is called "visual field". Nerve fibres from both eyes are divided so that fibers from the right half of both eyes reach the right half of the brain and fibers from the left half of both eyes the left half of the brain. See FIG. 2.

Figure 3:
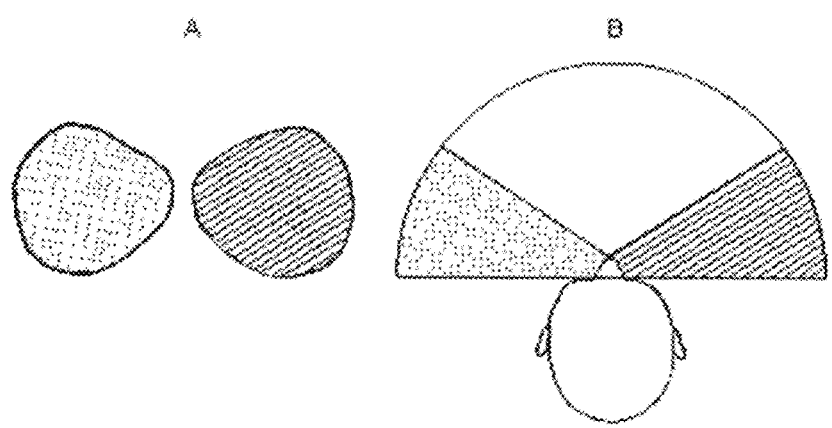
FIG. 3 illustrates visual field. 3A shows visual field of both eyes. 3B shows that the central part of the visual field (white area) is seen by both eyes.

Visual information coming from both eyes is fused in the visual cortex in the back of the brain. The central part of the visual field is seen by both eyes (FIG. 3). On both sides of this central, binocular field there are half moon formed parts of visual field that are seen by only one eye. See FIG. 3.

We use our peripheral or side vision when moving around. The most central part of the visual field is used in sustained near work, e.g., reading. When the visual field is measured with the clinical instruments these instruments measure what the weakest light is that the eye still can see in different parts of the visual field. A measurement like this gives valuable information on diseases of the visual pathways related to glaucoma or neurologic diseases. It does not give information on how the person sees forms or perceives movement in the different parts of the visual field.

The visual field can change in many ways. Therefore it is often difficult to understand how a visually impaired person sees. If the side parts of the visual field function poorly the person may need to use a white cane in order to move around safely, but (s)he may be able to read without glasses. On the other hand, if the side parts function well and the central field functions poorly, the person may walk like a normally sighted person, but may be able to read only the headings of a newspaper.

Figure 4:
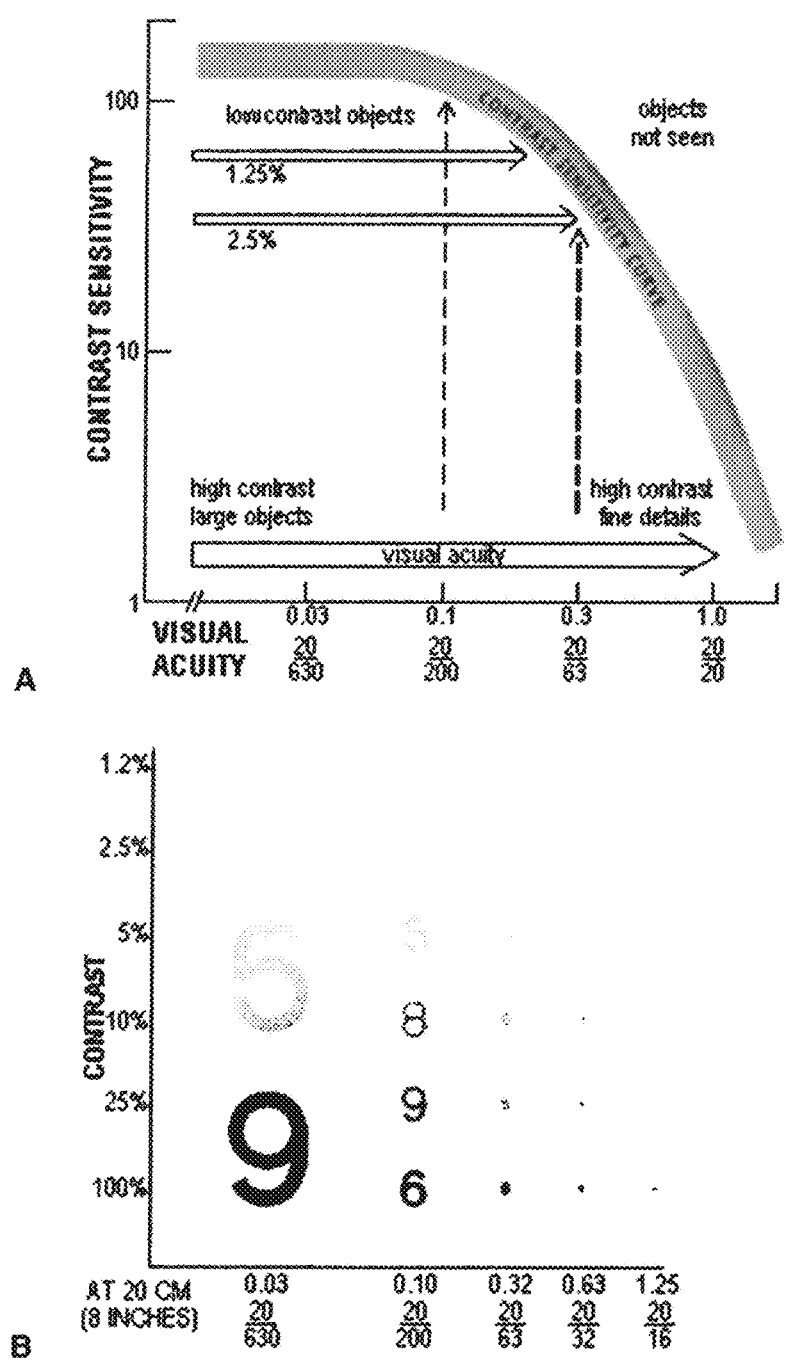
FIG. 4 illustrates contrast sensitivity. 4A shows the contrast sensitivity curve. 4B shows visual information at different contrasts in different sizes. Note that large numbers are visible at a fainter contrast than smaller numbers.

"Contrast sensitivity" can be depicted, for example, by a curve (See FIG. 4A). Under the curve there are the objects that we can see, above and to the right of the slope of the curve is the visual information that we cannot see. Contrast sensitivity can be measured using striped patterns, gratings, or symbols at different contrast levels.

When we measure hearing, an audiogram depicts which are the weakest tones at different frequencies that we still can hear. The measurements are made at low, intermediate and high frequencies. When we measure contrast sensitivity we measure what is the faintest grating or symbol still visible when the symbols are large, medium size or small (FIG. 4B).

If a visually impaired person has poor contrast sensitivity (s)he cannot see small contrast differences between adjacent surfaces. Everything becomes flat. It is difficult to perceive facial features and expressions. Text in the newspapers seems to have less contrast than before and it is difficult to recognize the edge of the pavement and the stairs.

Contrast sensitivity decreases in several common diseases, diabetes, glaucoma, cataract and diseases of the optic nerve.

Visual adaptation to different luminance levels: A normally sighted person can read by one candle's light and (s)he can read in bright sun light. The difference in the amount of light present in these two situations is million times. The normal person can adapt his/her vision to function at the different luminance levels.

The rod cells of the retina see best in twilight. If they do not function, the person is night blind. Night blindness is the first symptom that develops in many retinal diseases. First the child with a retinal disease starts to see in dim light after an abnormally long waiting. Therefore (s)he will have difficulties in finding his/her clothing in a closet or in a drawer if there is no extra illumination directed into these places. Later (s)he loses night vision completely, even when waiting for a long time (s)he does not start to see in the dark. Changes in visual adaptation time can be easily detected with the CONE Adaptation Test.

Photophobia and delayed adaptation to bright light are often additional symptoms of abnormal visual adaptation. When normally sighted persons enter from a darker room into a bright light, they also see very little for a second, sometimes it even hurts their eyes. They are dazzled. A visually impaired person may be dazzled for a long time. It is possible to decrease the problem by using absorptive glasses and a hat with wide brim or a visor.

Color Vision:

There are three different types of the retinal cone cells: some cells are most sensitive to red light, other to green light and the third type is most sensitive to blue light. Also the "normally sighted" individuals may have minor difficulties with color perception. It is often called color blindness but the term is poorly chosen because these persons are not blind, many of them are unaware that they have anything abnormal with their vision. However, if they compare such colors as moss green, snuff brown, dark purple, and dark grey, all these color may look more or less the same. Small deviations from normal affect only some specific working conditions. That is why color vision is examined at school before students get advice in career planning.

The screening examination uses pseudoisochromatic plates. Most commonly used test is called Ishihara's test. Screening tests are very sensitive and detect even minor deviations from normal color perception. They do not measure the degree of deviation. For the diagnosis of deviant color perception another test is necessary, a quantitative test in form of small caps with color surfaces in all colors of the spectrum. The diagnosis of color deficiency should never be based on a screening test. If a child seems to have any confusion with colors, color vision should be examined carefully. It can be started with clear basic colors to teach the concepts similar/different in relation to colors, after which quantitative testing is possible. Young children may train for the quantitative test by playing the Color Vision Game. Major color vision deficiencies are revealed already in this game but the diagnose requires proper measurement using pigment tests.

Binocular Vision and Three Dimensional Vision:

We have two eyes but see only one picture, image. Visual information coming from the two eyes is fused into one image in the visual cortex. Not all normally sighted have binocular vision. They do not use both eyes simultaneously, together. Some persons look alternatingly with their right or left eye. They are usually unaware that they use their eyes separately. It does not disturb them.

Stereovision or three dimensional vision means that we have depth perception in near vision. When we look far away we have another kind of depth perception. We pay attention to the relative size of objects and which object is partially hidden behind another object. The speed of movement with which an object seems to move when we move our head or move around (called parallax) gives us clues on the distance. Therefore persons who do not have stereovision can still assess depth.

Dominant Eye:

Dominant or leading eye is the eye that we use when we look very carefully at near or at far and can use only one eye. Even when both eyes are used simultaneously one of the eyes is more dominant than the other. We have hand, foot, and eye preference.

Figure 5:
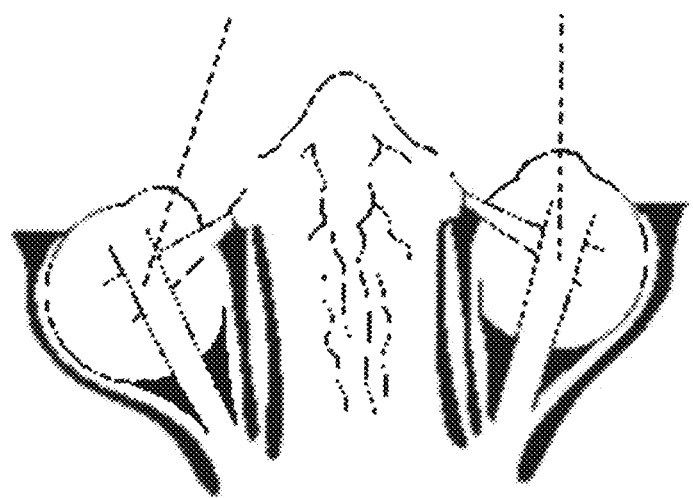
FIG. 5 illustrates eye muscles seen from above. The left outer muscle has developed palsy, the left eye turns inward.
Figure 6:
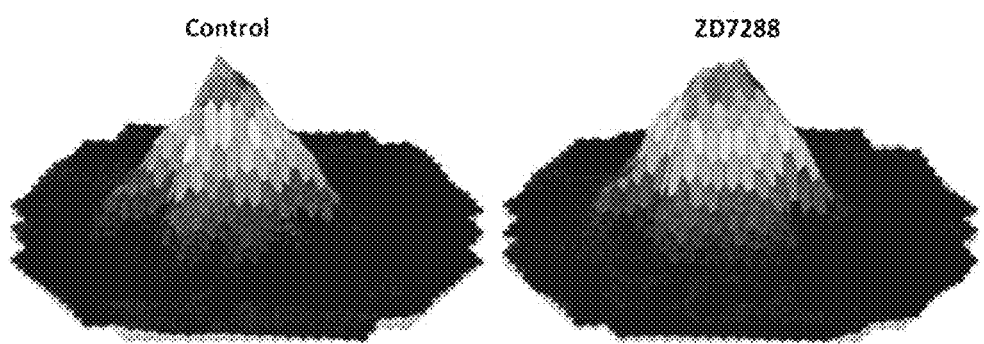
FIG. 6 illustrates RGC profile changes due to ZD7288. As observed in the receptive field profile of RGC in the figure, ZD7288 enhances the response near the receptive field center without affecting the surround.
Figure 7:
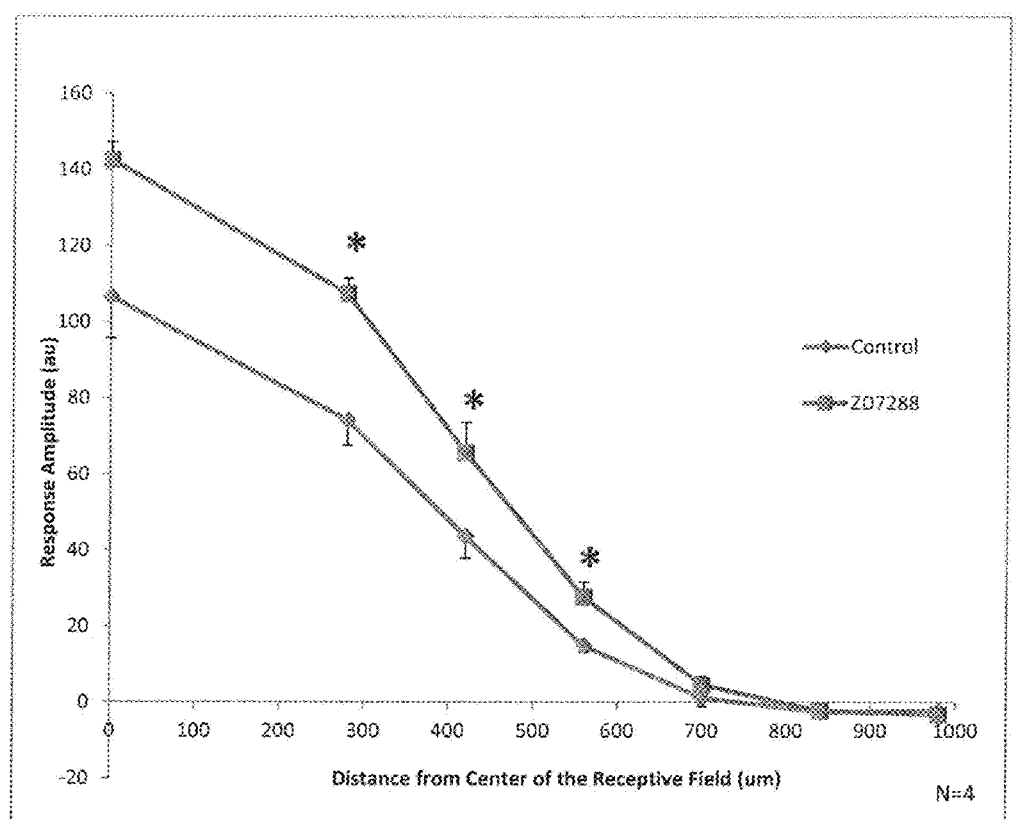
FIG. 7 shows the effects of 1 uM ZD7288 on OFF retinal ganglion cell receptive field profile using multifocal stimulus probe. The receptive field profile of OFF RGCs under control conditions and in the presence 1 uM ZD7288 and 1 uM ZD7288. ZD7288 significantly enhanced the receptive field profile of RGCs near the center of the receptive field.
Figure 8:
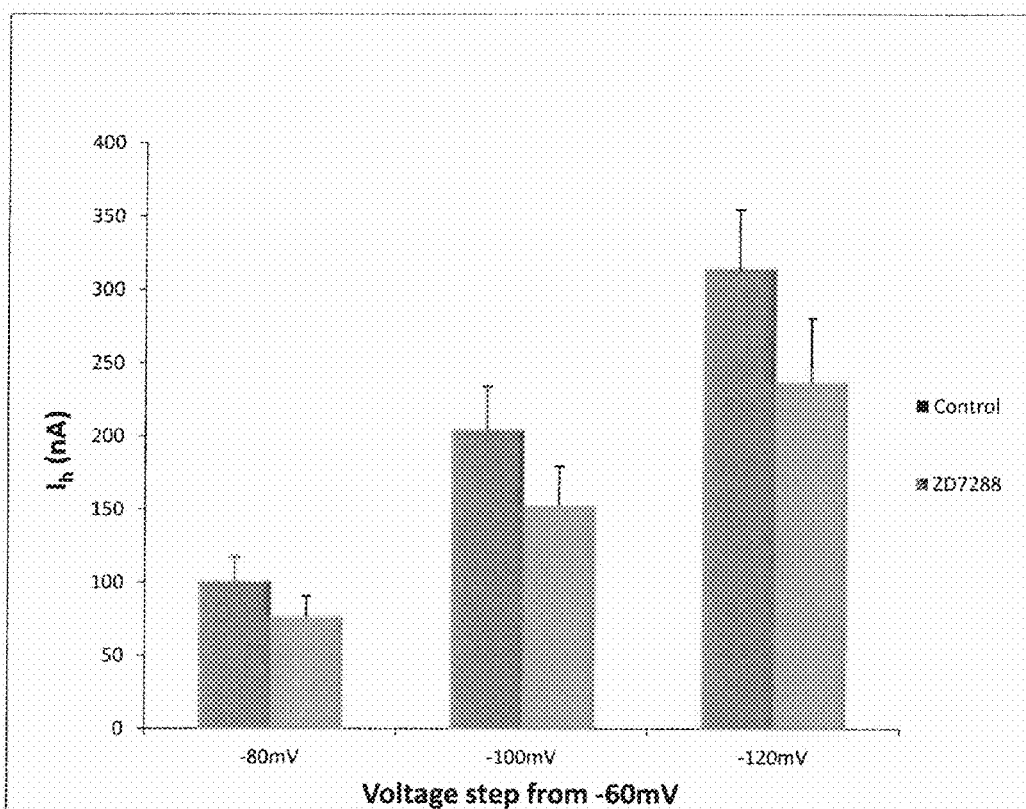
FIG. 8 shows the effects of 5 uM ZD7288 on retinal ganglion cell HCN current. HCN mediated Ih current was attenuated by ZD7288. All data were significantly different ($p<0.05$) as compared to control (N=6).
Figure 9:
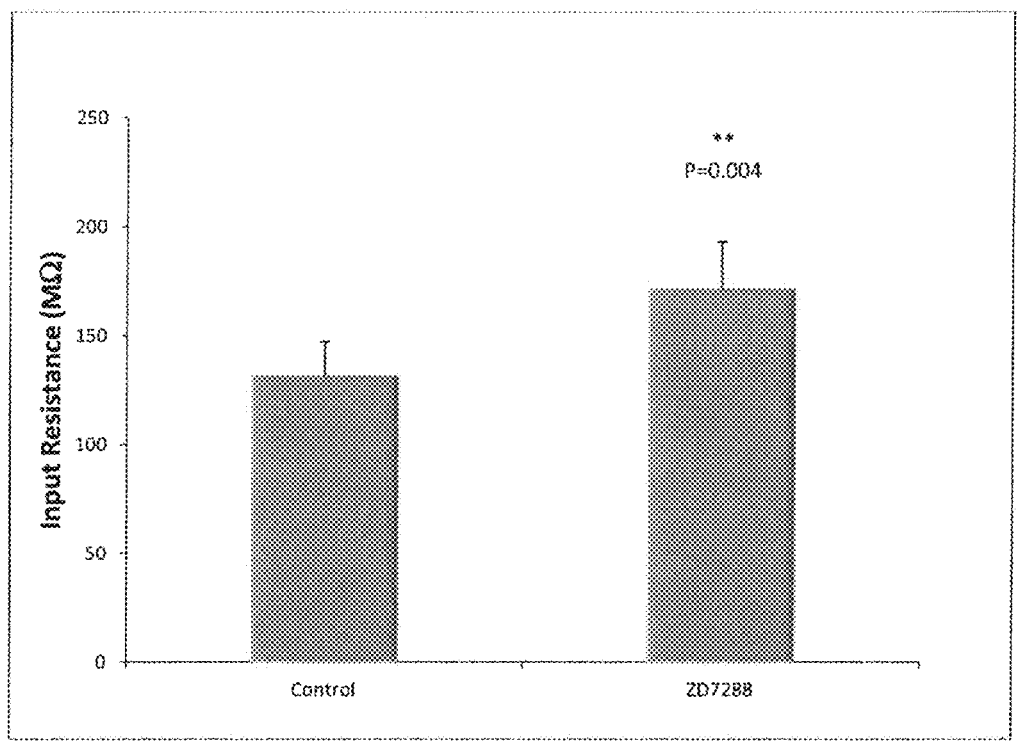
FIG. 9 shows the effects of 5 uM ZD7288 on retinal ganglion input resistance. It was hypothesized that HCN mediated Ih current gives rise to a leak conductance in retinal ganglion cells and blockade of this conductance would give rise to increased input resistance in these cells. The data clearly showed an enhancement of input resistance in ganglion cell (P<0.05, N=6).
Figure 10:
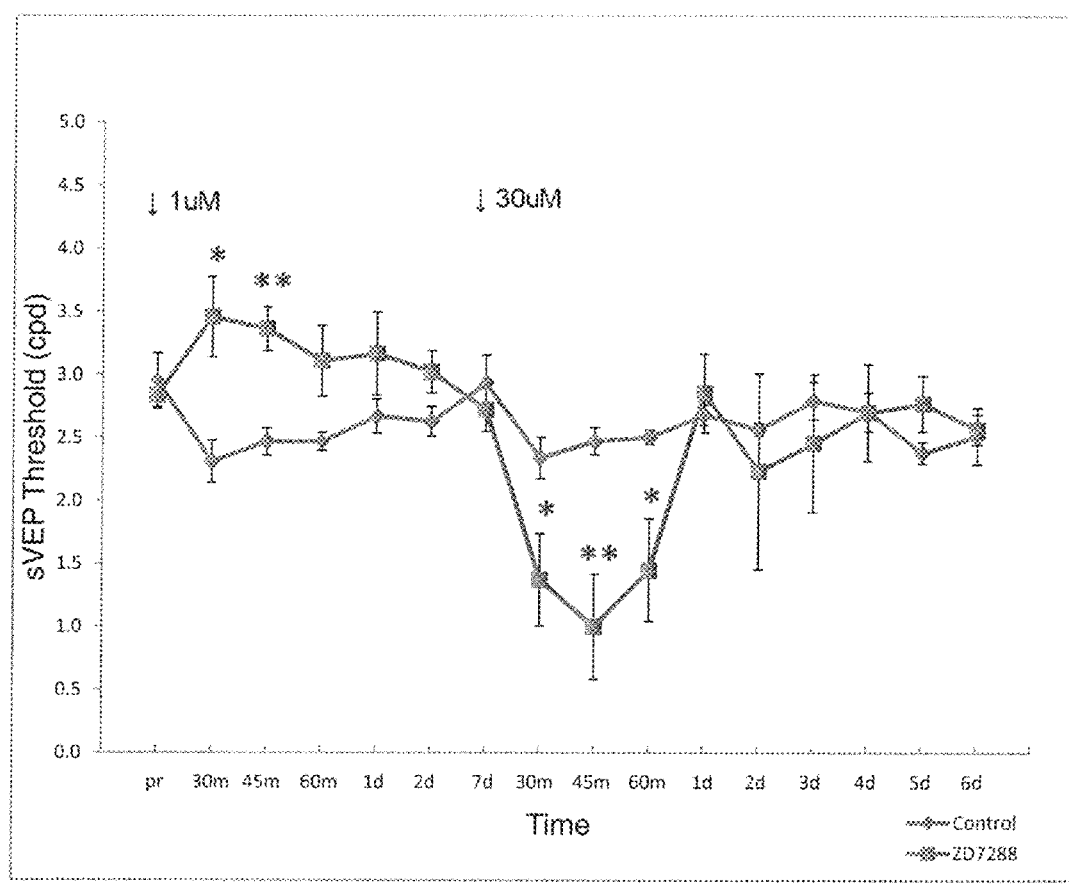
FIG. 10 shows the effects low (1 uM) and high (30 uM) ZD7288 on sweep vision evoked potential (VEP). Intravitreal dosing of rabbit with different doses of ZD7288 gave rise to opposite effects on sweep VEP acuity. At a low intravitreal dose of 1 uM, sweep VEP acuity was enhanced whereas at a high dose of 30 uM, sweep VEP acuity was attenuated (* P<0.05, N=4). The data strongly suggest that blockade of HCN channels with low doses targets the inner retina which gives rise to enhancement in acuity; whereas at higher doses, the outer retina is also affected because of better diffusion of the drug to the outer retina.

Eye Motility and its Disturbances:

Eye movements are usually well controlled. The eyes look at the same object. Eyes turn because of the function of six eye muscles. If one of the eye muscles is paralysed, the eye turns in an abnormal position, the person sees double images (FIG. 5)

If an eye muscle is not functioning properly the person sees double when trying to look in the direction where the muscle should function. When the eyes are turned in the opposite direction the double image is fused again. The eye with the disturbed motility is covered until the muscle function returns to normal.

Sometimes there is no disturbance in the muscles themselves but the command to turn eyes in a certain direction is not handled normally because of changes in brain function.

Variation in the Nature of Visual Disability:

Different visual functions may become impaired independent of each other. Therefore there are many different types of visual impairment and disability. Sometimes a visually impaired person seems to function in a very confusing way. One moment (s)he seems to function like a normally sighted person and in the next moment like a blind person. A visually impaired person seldom pretends to see less than what (s)he actually sees.

One reason for variation in visual behavior might be changes in illumination. Another may be that (s)he knows the surroundings so there is no difficulty in orientation. Normally sighted persons move about the same way at home in the dark. They move confidently and securely as long there is nothing unexpected in their way. If somebody leaves an object on the usual path they may trip over it. In the very same way a visually impaired person needs only a few visual cues in a well-known place in order to be able to move freely.

If it is difficult to understand how a visually impaired person sees it is quite proper to ask him/her about his/her vision. Most visually impaired people are able to describe the nature of their impairment so well that it is possible to understand their situation better. Some persons say that they have only 10% vision left. Such a number does not describe the degree of visual impairment. The person may be able to move freely relying on his/her vision or may function like a nearly blind. That number (10%) usually means that his/her visual acuity is 20/200 (6/60 or 0.1) and it describes only one of many visual functions.

If the loss of visual functioning is caused by brain damage, the behavior of the person may look even more perplexing than when the loss is caused by changes in the eyes. In the higher visual functions, perceptual functions, small specific areas of the brain cortex are responsible for specific perceptions. If such an area with specific function is damaged, the corresponding function is either weak or completely lost. Thus an otherwise normally sighted person may not recognize people, not even close relatives. (S)he sees faces but cannot connect the visual information with pictures of faces in his/her memory.

There can be an isolated loss of motion perception, so that the person cannot tell whether a car is moving or not, or in milder cases, may perceive some movement but not how fast the car may be approaching. Color perception may be disturbed. Recognition of geometric forms may be lost and thus learning letters and numbers may be impossible.

The structure of egocentric space may be lost and thus concepts like 'on the right', 'on the left', 'in the middle', 'next', may be difficult. Also drawing of simple pictures or even copying pictures of angles may be impossible.

It is important that these children/adult persons are not diagnosed as intellectually disabled if they have other functions where they function normally. An uneven profile of functions should always lead to a thorough assessment of all cognitive visual functions and auditory perception. Children with loss of recognition of facial features or facial expressions are sometimes diagnosed as autistic, which is a tragic error and may negatively affect the child's future.

In another embodiment of the invention, the inhibitor of the HCN channel is a selective inhibitor of HCN1 and/or HCN4.

In another embodiment, the inhibitor of the HCN channel is a selective inhibitor of HCN4.

In another embodiment, the HCN channel inhibitor is a selective bradycardic agent selected from the group consisting of alinidine (ST567), ZD-7288, zatebradine (UL-F549), cilobradine (DK-AH269), and ivabradine (Procorolan), or a pharmaceutically acceptable salt thereof.

Alinidine (ST567), available from Santa Cruz Biotechnology, Inc., is also known by the chemical names: —(N-Allyl-2,6-dichloroanilino)-2-imidazoline, and N-(2,6-dichlorophenyl)-4,5-dihydro-N-2-propenyl-1H-imidazol-2-amine; and has the chemical structure:

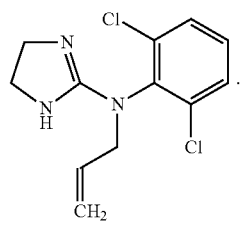 [SMILES: C=CCN(C1=NCCN1)c1c(Cl)cccc1Cl]

ZD 7288 (ICI D7288), in the form of the hydrochloride salt is available from Tocris Bioscience has the chemical name: 4-Ethylphenylamino-1,2-dimethyl-6-methylaminopyrimidinium chloride, and the chemical structure:

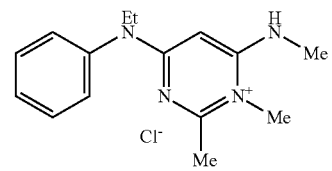

The term "ZD 7288" herein refers to base compound or any pharmaceutically acceptable salt of the base compound.

Zatebradine (UL-FS-49), has the chemical names: 3-(3-((3,4-Dimethoxyphenethyl)methylamino)propyl)-1,3,4,5-tetrahydro-7,8-dimethoxy-2H-3-benzazepin-2-one, and 3-[3-[2-(3,4-dimethoxyphenyl)ethyl-methylamino]propyl]-7,8-dimethoxy-2,5-dihydro-1H-3-benzazepin-4-one, and has the following chemical structure:

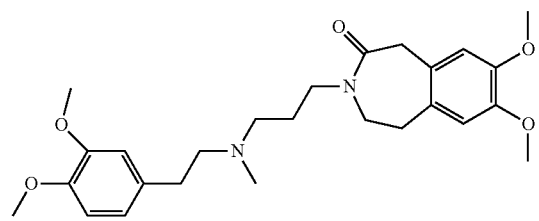

Zatebradine hydrochloride (the hydrochloride salt of zatebradine) is available from Tocris Bioscience and Sigma-Aldrich.

Cilobradine, available from Leancare Ltd., 2A Pharma-Chem USA and 3B Scientific Corporation, has following chemical structure:

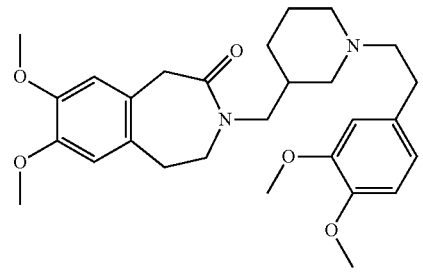 [SMILES: COc1ccc(CCN2CCCC(CN3CCc4cc(OC)c(OC)cc4CC3=O)C2)cc1OC]

Cilobradine hydrochloride, the hydrochloride salt of cilobradine (chemical name: (S)-(+)-7,8-Dimethoxy-3-[[1-(2-(3,4-dimethoxyphenyl)ethyl)-3-piperidinyl]methyl]-1,3,4,5-tetrahydro-2H-3-benzazepin-2-one hydrochloride), has the following chemical structure:

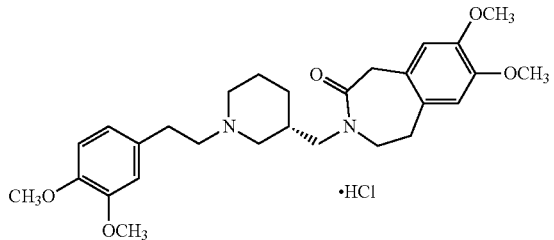

and is available from Sigma-Adrich.

Ivabradine has the chemical name: 3-[3-({[(7S)-3,4-dimethoxybicyclo[4.2.0]octa-1,3,5-trien-7-yl]methyl}(methyl)amino)propyl]-7,8-dimethoxy-2,3,4,5-tetrahydro-1H-3-benzazepin-2-one, and the chemical structure:

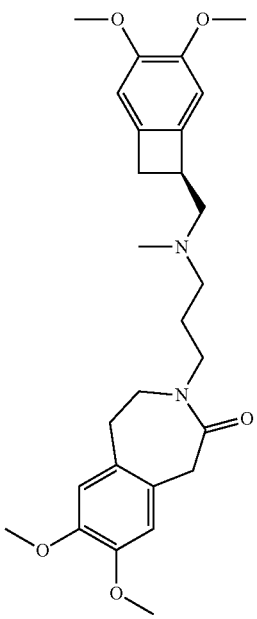 [SMILES: COc1cc2c(cc1OC)CC(=O)N(CCCN(C)C[C@H]1Cc3cc(OC)c(OC)cc31)CC2]

It is used for the symptomatic management of angina pectoris, and is marketed under the trade name "Procoralan" by Servier.

In another embodiment, the HCN channel inhibitor is an ivabridine derivative selected from the group consisting of MEL57A and EC18.

MEL57A has the following structure:

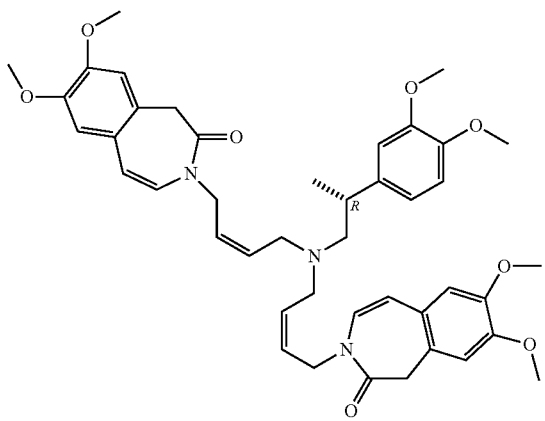

It's synthesis and pharmacological properties are disclosed in WO2011/000915A1.

EC18 has the following structure:

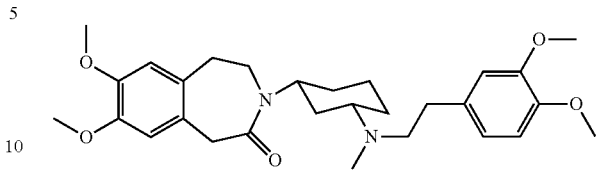

It's synthesis and pharmacological properties are disclosed in WO2011/000915A1.

In another embodiment, the HCN channel inhibitor is selected from the group consisting of ivabridine and ZD-7288.

In another embodiment, the visual function in the present invention is measured by sweep vision evoked potential (sVEP).

In another embodiment, the subject in need of the visual enhancement in the present invention is one who has low or poor visual function resulting from a retinal disorder or retinal damage.

In another embodiment, the ocular condition resulting from the low/poor visual function in the present invention is selected from the group consisting of glaucoma, low-tension glaucoma, intraocular hypertension, wet and dry age related macular degeneration (AMD), geographic atrophy, macula edema, Stargardt's disease cone dystrophy, and pattern dystrophy of the retinal pigmented epithelium, macular edema, retinal detachment and tears, retinal trauma, retinitis pigmentosa, retinal tumors and retinal diseases associated with said tumors, congenital hypertrophy of the retinal pigmented epithelium, acute posterior multifocal placoid pigment epitheliopathy, optic neuritis, acute retinal pigment epithelitis, diabetic retinopathy and optic neuropathies.

In another embodiment, the ocular condition resulting from the low/poor visual function in the present invention is selected from the group consisting of glaucoma, macular degeneration, wet and dry age related macular degeneration (AMD), geographic atrophy, and diabetic retinopathy.

In another embodiment, the administration of the HCN inhibitor enhances the receptive field profile of the retinal ganglion cells near the center of the receptive field.

In another embodiment, the administration of the HCN channel inhibitor attenuates HCN-mediated $I_h$ current.

In another embodiment, the administration of the HCN channel inhibitor results in an enhancement of input resistance in retinal ganglion cells by blockade of leak conductance in these cells.

The HCN-channel inhibitors of the present invention can form salts which are also within the scope of this invention. Reference to an HCN inhibitor herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when an HCN inhibitor contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the HCN inhibitors may be formed, for example, by reacting a such an antagonist with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

The compounds of the present invention can be administered in any one of conventional modes of pharmaceutical delivery, such as oral, intravenous, sublingual, intravitreal, topical, subcutaneous, trans-dermal, buccal, and intrathecal, or suitable combinations thereof. The topical and transdermal compositions can take the form of creams, lotions, aerosols and/or emulsions and can be included in a transdermal patch of the matrix or reservoir type as are conventional in the art for this purpose.

For preparing pharmaceutical compositions from the HCN-channel inhibitors described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

In addition to the common dosage forms set out above, the compounds of this invention may also be administered by controlled release means and/or delivery devices such as those described in U.S. Pat. Nos. 3,845,770; 3,916,899; 3,536,809; 3,598,123; 3,630,200; 4,008,719; and 5,366,738 the disclosures of which are incorporated herein by reference.

For use where a composition for intravenous administration is employed, a suitable daily dosage range for anti-inflammatory, anti-atherosclerotic or anti-allergic use is from about 0.001 mg to about 25 mg (preferably from 0.01 mg to about 1 mg) of a compound of this invention per kg of body weight per day and for cytoprotective use from about 0.1 mg to about 100 mg (preferably from about 1 mg to about 100 mg and more preferably from about 1 mg to about 10 mg) of a compound of this invention per kg of body weight per day. For the treatment of diseases of the eye, ophthalmic preparations for ocular administration comprising 0.001-1% by weight solutions or suspensions of the compounds of this invention in an acceptable ophthalmic formulation may be used.

Preferably, the pharmaceutical preparation is in a unit dosage form. In such form, the preparation is subdivided into suitably sized unit doses containing appropriate quantities of the active component, e.g., an effective amount to achieve the desired purpose.

The magnitude of prophylactic or therapeutic dose of a compound of this invention will, of course, vary with the nature of the severity of the condition to be treated and with the particular compound and its route of administration. It will also vary according to the age, weight and response of the individual patient. It is understood that a specific daily dosage amount can simultaneously be both a therapeutically effective amount, e.g., for treatment to slow progression of an existing condition, and a prophylactically effective amount, e.g., for prevention of condition. The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

In an especially preferred embodiment of this invention, the HCN-channel inhibitor of this invention is administered intraviteally (e.g., by injection into the back of the eye).

For intravitreal administration, the weight of the device (i.e., drug plus carrier/vehicle/excipient) is typically 1 mg (which for example may be administered with a 22 G needle) and the drug load is normally 10-50%. The drug dose range for intravitreal administration is normally about 100-500 μg. However, the drug load can be stretched to 2-65%, i.e., a drug dose range of 20-650 μg can be used. However, the device weight may be 1.5 mg, and for this a drug dose range of 20-975 μg can be used.

Another way of intravitreal delivery is by injecting drug suspension formulation. For this, the dose range is 10-600 ug.

The intraocular implant of the present invention typically comprises a therapeutically effective amount of the presently disclosed HCN-channel inhibitor (the therapeutic component; the active pharmaceutical ingredient (API)), and a drug release sustaining polymer component associated with the therapeutic compound. As used herein, an "intraocular implant" refers to a device or element that is structured, sized, or otherwise configured to be place in an eye. Intraocular implants are generally biocompatible with physiological conditions of an eye and do not cause adverse side effects. Intraocular implants may be place in an eye without disrupting vision of the eye.

The implant may be solid, semisolid, or viscoelastic. The drug release sustaining component is associated with the therapeutic component to sustain release of an amount of the therapeutic component into an eye in which the implant is placed.

The therapeutic component may be released from the implant by diffusion, erosion, dissolution or osmosis. The drug release sustaining component may comprise one or more biodegradable polymers or one or more non-biodegradable polymers. Examples of biodegradable polymers of the present implants may include poly-lactide-co-glycolide (PLGA and PLA), polyesters, poly (ortho ester), poly(phosphazine), poly(phosphate ester), polycaprolactone, natural polymers such as gelatin or collagen, or polymeric blends. The amount of the therapeutic component is released into the eye for a period of time greater than about one week after the implant is placed in the eye and is effective in reducing or treating an ocular condition.

In one embodiment, the intraocular implant comprises a therapeutic component and a biodegradable polymer matrix. The therapeutic component is associated with a biodegradable polymer matrix that degrades at a rate effective to sustain release of an amount of the therapeutic component from the implant effective to treat an ocular condition. The intraocular implant is biodegradable or bioerodible and provides a sustained release of the therapeutic component in an eye for extended periods of time, such as for more than one week, for example for about one month or more and up to 5 about six months or more. The implant may be configured to provide release of the therapeutic component in substantially one direction, or the implant may provide release of the therapeutic component from all surfaces of the implant.

The biodegradable polymer matrix of the foregoing implant may be a mixture of biodegradable polymers or the matrix may comprise a single type of biodegradable polymer. For example, the matrix may comprise a polymer selected from the group consisting of polylactides, poly(lactide-co-glycolides), polycaprolactones, and combinations thereof.

In another embodiment, the intraocular implant comprises the therapeutic component and a polymeric outer layer covering the therapeutic component. The polymeric outer layer includes one or more orifices or openings or holes that are effective to allow a liquid to pass into the implant, and to allow the therapeutic component to pass out of the implant.

The therapeutic component is provided in a core or interior portion of the implant, and the polymeric outer layer covers or coats the core. The polymeric outer layer may include one or more non-biodegradable portions. The implant can provide an extended release of the therapeutic component for more than about two months, and for more than about one year, and even for more than about five or about ten years. One example of such a polymeric outer layer covering is disclosed in U.S. Pat. No. 6,331,313.

In one embodiment, the present implant provides a sustained or controlled delivery of the therapeutic component at a maintained level despite the rapid elimination of the therapeutic component from the eye. For example, the present implant is capable of delivering therapeutically effective amounts of the therapeutic component for a period of at least about 30 days to about a year despite the short intraocular half-lives that may be associated with the therapeutic component. Plasma levels of the therapeutic component obtained after implantation may be extremely low, thereby reducing issues or risks of systemic toxicity. The controlled delivery of the therapeutic component from the present implants would permit the therapeutic component to be administered into an eye with reduced toxicity or deterioration of the blood-aqueous and blood-retinal barriers, which may be associated with intraocular injection of liquid formulations containing the therapeutic component.

A method of making the present implant involves combining or mixing the therapeutic component with a biodegradable polymer or polymers. The mixture may then be extruded or compressed to form a single composition. The single composition may then be processed to form individual implants suitable for placement in an eye of a patient.

Another method of making the present implant involves providing a polymeric coating around a core portion containing the therapeutic component, wherein the polymeric coating has one or more holes. The implant may be placed in an ocular region to treat a variety of ocular conditions, such as treating the conditions disclosed herein.

The daily dose may be administered as single dose or in divided doses and, in addition, the upper limit can also be exceeded when this is found to be indicated Assays Retinal Ganglion Cell Receptive Field Recordings. Six month old male Dutch belted rabbits were anesthetized using intramuscular injection of ketamine and were placed under deep isofluorane anesthesia. The eyes were enucleated under dim lighted conditions and transferred to a dark room where the anterior of the eye along with the vitreous humor were removed. An 11 mm circular punch of the central retina, below the optic nerve head, was made and the inverted eyecup preparation with the ganglion-cell layer facing upward was transferred to the recording chamber. The retina was dark adapted for one hour and subsequently experiments were performed in the dark at 35° C. Following enucleation, the animals were euthanized with an intravenous injection of euthasol. All animal procedures conformed to the Allergan Animal Care and Use Committee.

The retinal preparation was continuously perfused with Ames' solution saturated with 95% $O_2$ and 5% $CO_2$ maintained at a pH of 7.4. Receptive fields profiles of retinal ganglion cells were probed using the VERIS™ multifocal stimulus and analysis system. 2 ms white light flashes (hexagons at 140 μm in diameter) were induced using m-sequence stimulation at the beginning of each frame with a 38 ms delay between flashes at an intensity of $7.56 \times 10^9$ hv/flash·$cm^2$. Data analysis of the ganglion cell receptive field was performed using VERIS™ (EDI, Redwood City, Calif.).

HCN channel Current (Ih) and Input Resistance Measurements.

Isolated retina preparations were made from 6 to 12 month old Brown Norway rats following decapitation. All animal procedures conformed to the Allergan Animal Care and Use Committee. The retina was transferred to a recording chamber with the retinal ganglion cell layer facing up and individual cells were patch clamped for voltage clamp recordings. A combination of 100 uM Picrotoxin and 20 uM DNQX were perfused into the chamber to isolate ganglion cell responses from presynaptic cells. The membrane potential of ganglion cells were clamped at −60 mV and a 10 ms 5 mV depolarizing step at the beginning of the recording was made to measure the cells input resistance followed by 1 second step to −80, −100 and −120 mV to measure the HCN mediated Ih current. Following control recordings, ZD7288 and Ivabradine (see figures for concentrations) were perfused into the recording chamber and the electrophysiological measures were repeated to assess the effects of the drugs on input resistance and Ih.

Sweep Vision Evoked Potential (sVEP) Measurements.

sVEP is an indirect measure of visual acuity and is highly correlated with snellen acuity in humans (Ridder 2004). sVEP is a tool that is often used to assess visual function in human infants and animal models since these subjects can't read a Snellen chart or communicate with the test administrator (Norcia et al., 1985; Guire et al., 1999). sVEP measurements were made from awake Dutch-belted rabbits using a spatial frequency range from 0.3 to 5 cycles per degree at 80% contrast using the Power-Diva system. Following control recordings, an intravitreal injection of 1 uM ZD7288 was made and the recording was repeated for 7 days post injection (see figure for more details). After the response returned to baseline a 30 uM intravitreal dose of ZD7288 was made and the measurements were repeated for 6 days post injection (see figure for more details). 50 uL Intravitreal injections of concentrated dose (24 fold to account for rabbit vitreal dilution) of the drug were made with a 30 gauge hypodermic needle and a Hamilton syringe.

What is claimed is:

1. A method of enhancing visual function in a subject, comprising administering to the subject in need of such enhancement, a therapeutically effective amount of an inhibitor of a hyperpolarization-activated cyclic nucleotide-gated (HCN) channel.

2. The method of claim 1, wherein the visual function is selected from the group consisting of visual acuity, visual field, contrast sensitivity, visual adaptation to different luminance levels, color vision, binocular and three dimensional vision.

3. The method of claim 2, wherein the visual function is visual acuity.

4. The method of claim 1, wherein the inhibitor is a selective inhibitor of HCN1 and/or HCN4.

5. The method of claim 1, wherein the inhibitor is a selective bradycardic agent selected from the group consisting of alinidine (ST567), ZD-7288, zatebradine (UL-F549), cilobradine (DK-AH269), and ivabradine (Procorolan); an ivabridine derivative selected from the group consisting of MEL57A and EC18; or a pharmaceutically acceptable salt of any of the above.

6. The method of claim 1, wherein the subject in need of such enhancement is one who has low/poor visual function resulting from a retinal disorder or retinal damage.

7. The method of claim 3, wherein said visual acuity is measured by sweep vision evoked potential (sVEP).

8. The method of claim 1, wherein administration of the compound enhances the receptive field profile of the retinal ganglion cells near the center of the receptive field.

9. The method of claim 1, wherein administration of the inhibitor attenuates HCN-mediated $I_h$ current.

10. The method of claim 1, wherein administration of the inhibitor results in an enhancement of input resistance in retinal ganglion cells by blockade of leak conductance in these cells.

11. The method of claim 1, wherein the HCN-channel inhibitor is administered intravitreally.

12. A method of treating an ocular condition resulting from low/poor visual function in a subject, comprising administering to said subject in need of such treatment, a therapeutically effective amount of an inhibitor of a hyperpolarization-activated cyclic nucleotide-gated (HCN) channel.

13. The method of claim 12, wherein said ocular condition is selected from the group consisting of glaucoma, low-tension glaucoma, intraocular hypertension, age related macular degeneration (AMD) (including wet and dry AMD), geographic atrophy, macula edema, Stargardt's disease cone dystrophy, and pattern dystrophy of the retinal pigmented epithelium, macular edema, retinal detachment and tears, retinal trauma, retinitis pigmentosa, retinal tumors and retinal diseases associated with said tumors, congenital hypertrophy of the retinal pigmented epithelium, acute posterior multifocal placoid pigment epitheliopathy, optic neuritis, acute retinal pigment epithelitis, diabetic retinopathy and optic neuropathies.

14. The method of claim 12, wherein the inhibitor is a selective inhibitor of HCN1 and/or HCN4.

15. The method of claim 12, wherein the inhibitor is a selective bradycardic agent selected from the group consisting of alinidine (ST567), ZD-7288, zatebradine (UL-FS49), cilobradine (DK-AH269), and ivabradine (Procorolan); an ivabridine derivative selected from the group consisting of MEL57A and EC18; or a pharmaceutically acceptable salt of any of the above.

16. The method of claim 12, wherein the HCN-channel inhibitor is administered intravitreally.

17. An ocular implant comprising a therapeutically effective amount of an inhibitor of a hyperpolarization-activated cyclic nucleotide-gated (HCN) channel.

18. The implant of claim 17, wherein the inhibitor is a selective inhibitor of HCN1 and/or HCN4.

19. The implant of claim 17, wherein the inhibitor is a selective bradycardic agent selected from the group consisting of alinidine (ST567), ZD-7288, zatebradine (UL-F549), cilobradine (DK-AH269), and ivabradine (Procorolan); an ivabridine derivative selected from the group consisting of MEL57A and EC18; or a pharmaceutically acceptable salt of any of the above.

* * * * *